(12) United States Patent
Doehner, Jr.

(10) Patent No.: US 6,441,219 B1
(45) Date of Patent: Aug. 27, 2002

(54) PROCESS FOR THE PREPARATION OF 5- AND/OR 6-SUBSTITUTED-2-HYDROXYBENZOIC ACID ESTERS

(75) Inventor: Robert Francis Doehner, Jr., East Windsor, NJ (US)

(73) Assignee: BASF Corporation, Mount Olive, NJ (US)

( * ) Notice: Subject to any disclaimer, the term of this patent is extended or adjusted under 35 U.S.C. 154(b) by 0 days.

(21) Appl. No.: 09/699,775

(22) Filed: Oct. 30, 2000

Related U.S. Application Data

(63) Continuation-in-part of application No. 09/354,037, filed on Jul. 15, 1999, now abandoned.

(51) Int. Cl.$^7$ .............................................. C07C 69/88

(52) U.S. Cl. ........................................ 560/67; 568/333

(58) Field of Search ............................ 560/67; 568/333

(56) References Cited

U.S. PATENT DOCUMENTS

| | | |
|---|---|---|
| 3,846,497 A | 11/1974 | Himmele |
| 5,773,663 A | 6/1998 | Curtze et al. ................ 568/333 |
| 5,945,567 A | 8/1999 | Curtze et al. ................ 568/333 |

OTHER PUBLICATIONS

Snider, B et al, J. Org. Chem. (1988), 53(10), 2137–43.*
Snider, B et al J. Org. Chem (1989), 54(1) 38–46.*
G. Schill, et al. "Synthesis," Inter. Journal of Methods in Synthetic Organic Chemistry: 1980, 814–815.
Y. Hamada, et al. Tetrahedron, vol. 4, 8635–8652 (1991).
S. Sandler and J. W. Karo "Organic Functional Group Preparations" Acad. Press: NY: pp. 218–232.

* cited by examiner

*Primary Examiner*—Paul J. Killos
(74) *Attorney, Agent, or Firm*—Charles F. Costello

(57) ABSTRACT

There is provided a single-step process for the preparation of a compound of formula I.

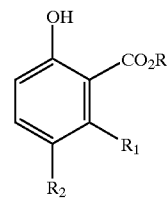

(I)

Compounds of formula I are useful as starting materials in the synthesis of natural products and in the manufacture of benzophenone fungicidal agents.

12 Claims, No Drawings

PROCESS FOR THE PREPARATION OF 5- AND/OR 6-SUBSTITUTED-2-HYDROXYBENZOIC ACID ESTERS

This application is a C-I-P of Ser. No. 09/354,037 filed Jul. 15, 1999, Abn.

BACKGROUND OF THE INVENTION

Derivatives of 2-hydroxybenzoic acid esters are useful starting materials for natural product synthesis, for example F. M. Hauser, et al., Synthesis 1980, 72 or for the manufacture of fungicidal benzophenones such as those described in U.S. Pat. No. 5,773,663. Methods to prepare said 2-hydroxybenzoic acid esters are known, i.e. G. Schill, et al., Synthesis, 1980, 814 or Y. Hamada, et al, Tetrahedron, Vol. 47 (1991), 8635. However, these known methods require several steps and utilize corrosive or toxic reagents and are not amenable to large scale preparation or commercial manufacturing conditions.

The two-step syntheses cited in Synthesis and Tetrahedron hereinabove require the isolation of intermediates resulting in an undue solvent waste load on the environment. Further these syntheses require gaseous HCl and a separate oxidation procedure employing oxidizing reagents such as $Br_2$ or $CuCl_2$.

Therefore, it is an object of this invention to provide an effective and efficient single-step process to prepare 5- and/or 6-substituted-2-hydroxybenzoic acid esters which is amenable to large scale preparations and commercial manufacturing procedures.

It is another object of this invention to provide an effective means of obtaining a substituted-2-hydroxy-benzoic acid ester in good yield under relatively mild reaction conditions from readily available starting materials and reagents.

It is a further object of this invention to provide an environmentally sound commercial source of substituted-2-hydroxybenzoic acid esters for the preparation of important phytopathogenic fungicidal agents and the continued exploration of natural product synthesis. These and other objects and features of the invention will become more apparent from the detailed description set forth hereinbelow.

SUMMARY OF THE INVENTION

The present invention provides a single-step process for the preparation of a compound of formula I

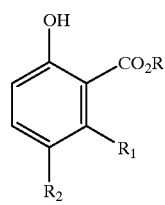

(I)

wherein

R is $C_1$–$C_6$alkyl; and $R_1$ and $R_2$ are each independently H or $C_1$–$C_4$alkyl which process comprises reacting a compound of formula II

(II)

wherein R is $C_1$–$C_6$alkyl and X is halogen or $OCOCH_3$ with a compound of formula III

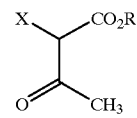

(III)

wherein $R_1$ and $R_2$ are each independently H or $C_1$–$C_4$alkyl, and formula III compound is understood to be cis, Trans, or a mixture thereof, in the presence of a $C_1$–$C_4$carboxylic acid salt and a solvent.

Also provided is the use of the formula I compound in the manufacture of a fungicidal benzophenone compound. In one embodiment, a process for the manufacture of a fungicidal benzophenone compound of formula K

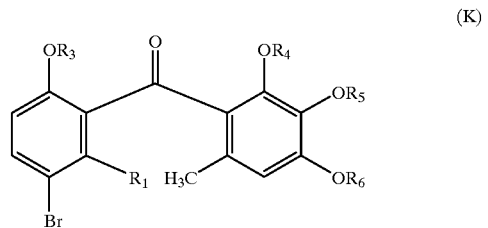

(K)

wherein $R_1$ is independently H or $C_1$–$C_4$alkyl; and $R_3$, $R_4$, $R_5$ and $R_3$, $R_4$, $R_5$ and $R_6$ are each independently $C_1$–$C_6$alkyl which process comprises the following steps:

a) reacting a compound of formula II

(II)

wherein R is $C_1$–$C_6$alkyl and X is halogen or $OCOCH_3$ with a compound of formula IIIA

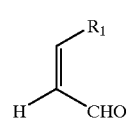

(IIIA)

wherein $R_1$ is as described hereinabove in the presence of a $C_1$–$C_4$ carboxylic acid salt and a solvent to form a compound of formula IA.

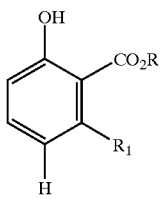

(IA)

wherein R, $R_1$ and $R_2$ are described hereinabove;

b) alkylating the formula I compound with a di($C_1$–$C_6$alkyl)sulfate in the presence of a base to form a compound of formula VA

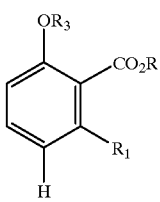

(VA)

wherein $R_3$ is $C_1$–$C_6$alkyl;

c) brominating the formula VA compound with a brominating agent such as bromine or N-bromosuccinimide, optionally in the presence of a base, to form a compound of formula L

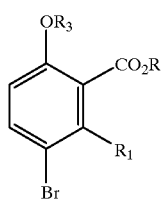

(L)

wherein R, $R_1$ and $R_3$ are described hereinabove;

d) hydrolyzing the formula L compound in an aqueous acid or aqueous base to form a compound of formula M

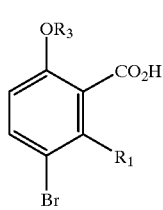

(M)

wherein $R_1$ and $R_3$ are described hereinabove;

e) reacting the formula M compound with thionyl chloride to form the compound of formula N

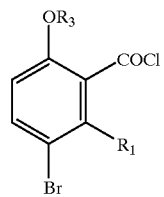

(N)

wherein $R_1$ and $R_3$ are described hereinabove; and f) reacting the formula N compound with at least one molar equivalent of a compound of formula VIII

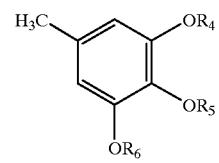

(VIII)

wherein $R_4$, $R_5$ and $R_6$ are each independently $C_1$–$C_6$alkyl, in the presence of a solvent, to give the desired fungicidal formula K benzophenone compound.

DETAILED DESCRIPTION OF THE INVENTION

Substituted-2-hydroxybenzoic acid esters of formula I are useful as key starting materials in natural product synthesis and in the manufacture of important benzophenone fungicidal agents. Said fungicidal agents help growers provide top quality food products and feed grains to U.S. consumers as well as the world. Virtually all seeds for U.S. corn and wheat crops and nearly one-third of soybeans are treated with fungicidal agents. Therefore, the efficient preparation of such fungicidally active compounds in an environmentally sound manner is highly desirable.

It has now been found that 5- and/or 6-substituted-2-hydroxybenzoic acid esters of formula I may be prepared in a single-step process from readily available starting materials and under relatively mild reaction conditions, allowing effective large scale commercial production. Advantageously, the process of the invention avoids the use of corrosive gaseous HCl and eliminates the need for oxidizing reagents such as $Br_2$ and $CuCl_2$.

Preferred compounds prepared by the process of the invention are those compounds of formula I wherein $R_1$ is $C_1$–$C_4$alkyl and $R_2$ is hydrogen. More preferred compounds are those compounds of formula I wherein $R_1$ is methyl and $R_2$ is hydrogen.

Preferred compounds of formula II employed in the process of the invention are those compounds wherein X is halogen. More preferred compounds are those compounds of formula II wherein X is Cl.

Compounds of formula III may be represented in the cis or trans configuration or as a mixture thereof. In the specification and claims, compounds designated as formula III include the cis isomer, the trans isomer or a mixture thereof.

The term halogen as used in the specification and claims designates Cl, Br, F or I.

In accordance with the process of the invention, a β-ketoester of formula II is reacted with an α,β-unsaturated aldehyde of formula III in the presence of a $C_1-C_4$carboxylic acid salt, preferably about 1.0–2.0 molar equivalents, more preferably about 1.0–1.5 molar equivalents and a solvent, preferably a $C_1-C_6$alkanol, a $C_1-C_4$ carboxylic acid or a mixture thereof, more preferably methanol, ethanol, acetic acid or a mixture thereof to form the desired product of formula I. The reaction is shown in flow diagram I wherein M is an alkali metal or an alkaline-earth metal.

Flow Diagram I

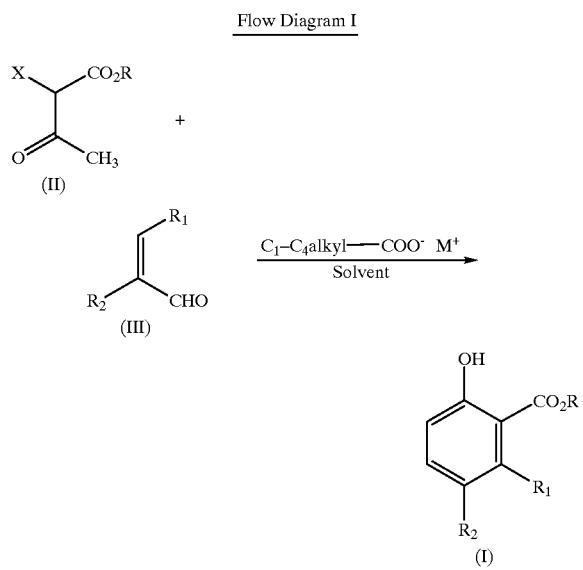

The formula I hydroxybenzoic acid ester product may be isolated using conventional isolation techniques such as precipitation, decantation, filtration, extraction, chromatographic separation or the like, preferably filtration or extraction.

In the process of the invention, reaction rate is directly related to reaction temperature, that is, the reaction rate increases with increased temperature. However, excessively high reaction temperatures may lead to decomposition and the formation of undesired by-products, thereby reducing product yield and purity. Suitable reaction temperatures in the process of the invention may range from room temperature to the reflux temperature of the solvent preferably about 25° C. to 125° C., more preferably about 75° to 120°.

Acid salts suitable for use in the process of the invention are aliphatic acid salts, preferably $C_1-C_4$-carboxylic acid alkali metal or alkaline-earth salts, more preferably acetic acid alkali metal salts such as sodium acetate or potassium acetate.

Suitable solvents for use in the inventive process include polar solvents, preferably protic solvents such as $C_1-C_6$alkanols, $C_1-C_4$carboxylic acids or a mixture thereof, more preferably methanol, ethanol, acetic acid or a mixture thereof.

In actual practice, the formula II β-ketoester and the formula III α,β-unsaturated aldehyde are admixed with about 1.0 to 2.0, preferably about 1.0 to 1.5, more preferably about 1.2, molar equivalents of a $C_{1-C4}$carboxylic acid salt, preferably an alkali metal or an alkaline-earth metal salt, more preferably an alkali metal acetate in a solvent, preferably a protic solvent, more preferably a $C_1-C_4$alkanol, a $C_1-C_4$carboyxic acid or a mixture thereof, at room temperature to the reflux temperature of the solvent, preferably 25° C. to 125° C., more preferably 75° C. to 120° C. to form the desired formula I 5- and/or 6-substituted-2-hydroxybenzoic acid ester.

Compounds of formula I are useful as intermediates in the synthesis of natural products and in the manufacture of benzophenone fungicidal agents. Accordingly, in one embodiment of the invention a compound of formula I prepared from the compounds of formula II and III in a single-step procedure as described hereinabove may be conveniently converted to a benzophenone fungicidal compound of formula IV by alkylating the formula I compound with a di-($C_1-C_6$alkyl)sulfate in the presence of a base to form the corresponding alkoxy derivative of formula V; hydrolyzing the formula V derivative in the presence of aqueous acid or aqueous base to form the corresponding formula VI carboxylic acid; reacting the formula VI compound with a chlorinating agent such as $SOCl_2$ to form the acid chloride of formula VII; and reacting the formula VII acid chloride with a compound of formula VIII in the presence of a Lewis acid, optionally in the presence of a solvent, to form the desired formula IV fungicidal product. The reaction sequence is shown in flow diagram II wherein $R_3$, $R_4$, $R_5$ and $R_6$ are each independently $C_1-C_6$alkyl. Alternatively, as shown in flow diagram III, where $R_2$ is hydrogen in formulae I, III and V, a halogenation step, for example bromination, can be used after the alkylation step.

Flow Diagram II

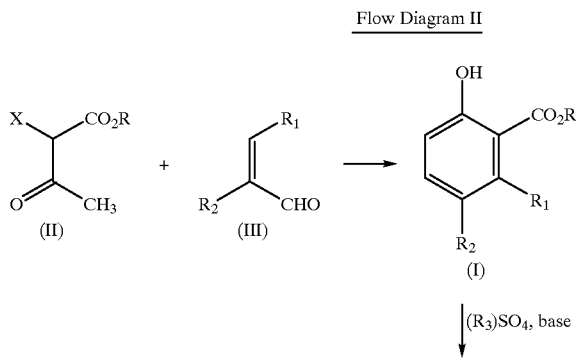

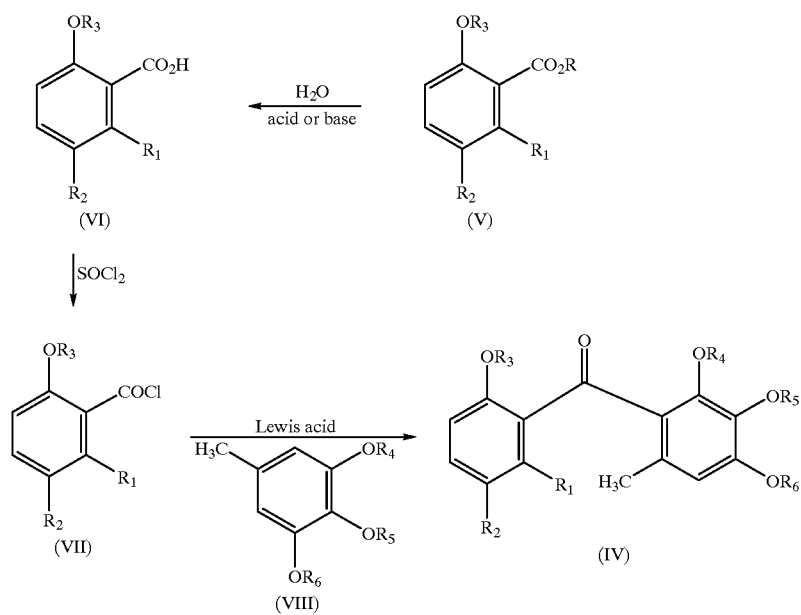
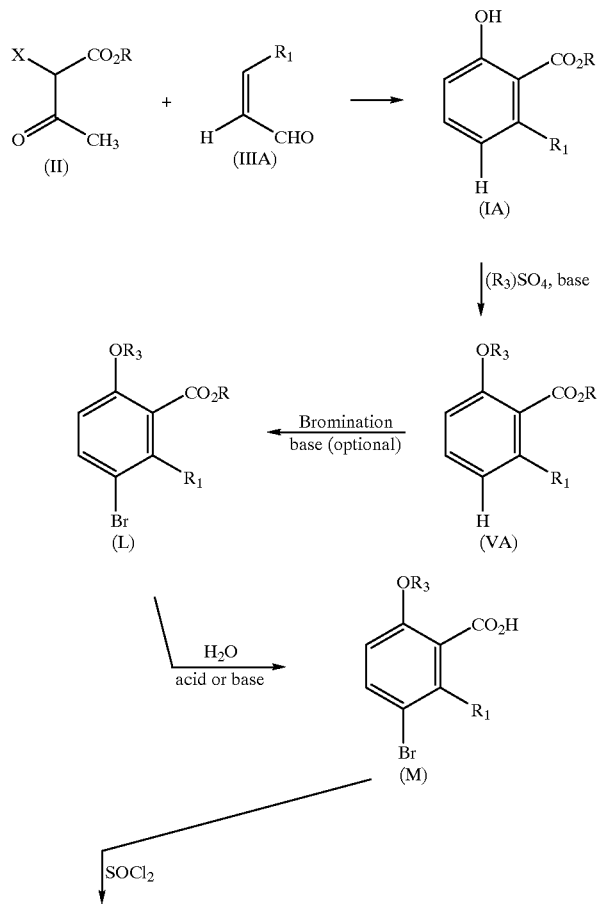
Flow Diagram III

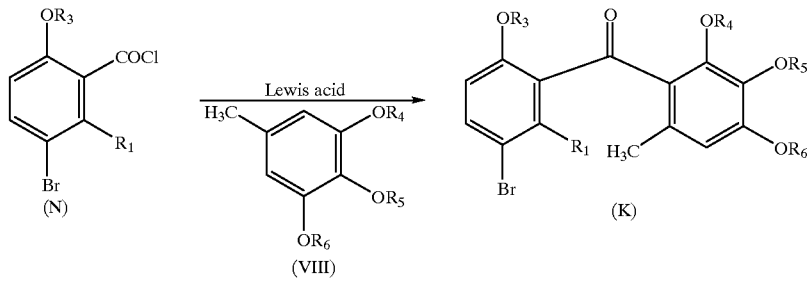

Referring to flow diagrams II and III, and not being bound by any theory, the reaction of a formula II compound with a formula III compound probably involves a Michael condensation to give the desired formula E compound. An internal Aldol reaction of the formula E compound generates a compound of formula F, followed by dehydration to a compound of formula G. Finally, dehydrohalogenation of a compound of formula G gives the desired compound of formula I.

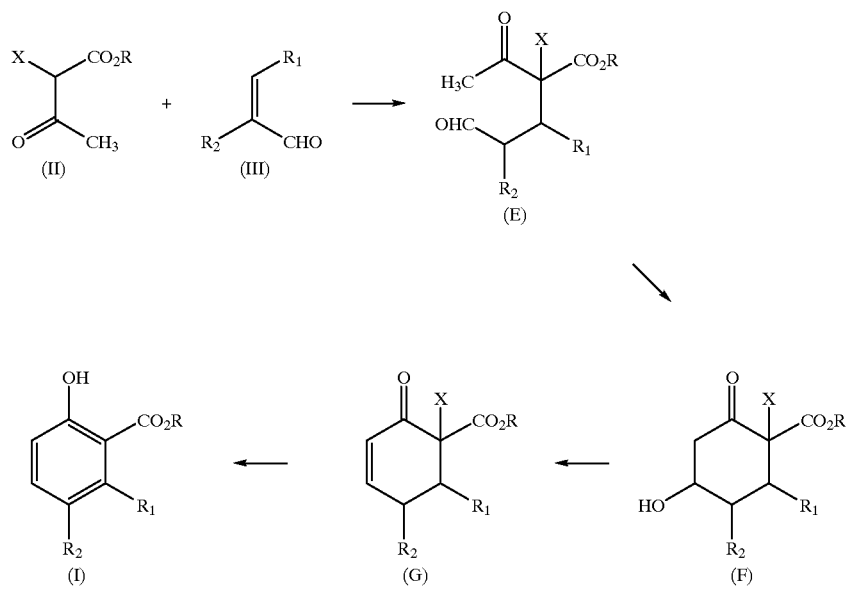

Compounds of formula IV, their fungicidal use and methods to prepare compounds of formula IV are described in U.S. Pat. No. 5,773,663, incorporated herein by reference thereto.

For a more clear understanding of the invention, the following examples are set forth below. These examples are merely illustrative and are not be understood as limiting the scope or underlying principles of the invention in any way.

The term NMR designates nuclear magnetic resonance spectroscopy. Unless otherwise mentioned, all parts are parts by weight.

EXAMPLE 1

Preparation of Ethyl 2-Hydroxy-6-methylbenzoate

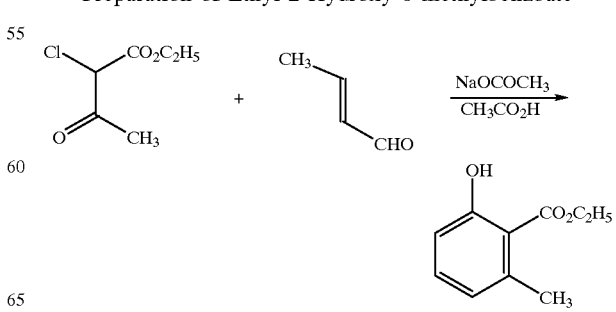

A stirred mixture of crotonaldehyde (21.0 g, 0.30 mol) and anhydrous sodium acetate (25.0 g, 0.30 mol) in glacial acetic acid is heated to reflux temperature under $N_2$, treated dropwise with ethyl chloroacetoacetate (41.1 g, 95%, 0.25 mol) over a 2.25 hr. period, heated at reflux temperature for 16 hr., cooled to room temperature and concentrated in vacuo to give a residue. The residue is partitioned between ethyl acetate and water. The organic phase is diluted with hexanes, washed sequentially with water and aqueous $NaHCO_3$ and concentrated in vacuo to give the title product as an oil, 41.0 g, 71.4% purity (65% yield), characterized by NMR analysis.

EXAMPLE 2

Preparation of Ethyl 2-Hydroxy-5-methylbenzoate

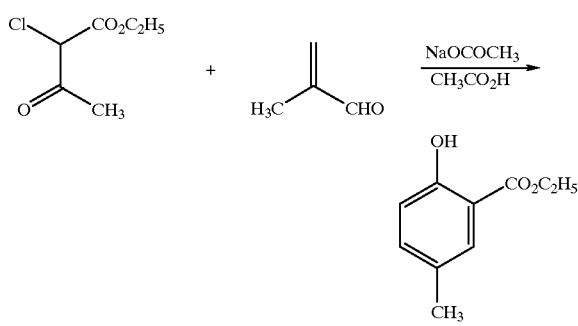

A stirred mixture of 2-methylacrolein (22.8 g, 92%, 0.30 mol), ethyl 2-chloroacetoacetate (41.1 g, 95%, 0.25 mol) and anhydrous sodium acetate (24.6 g, 0.30 mol) in acetic acid is heated at reflux temperature under $N_2$ for 16 hr., cooled to room temperature and concentrated in vacuo to give a residue. The residue is partitioned between ethyl acetate and water. The organic phase is concentrated in vacuo to give the title product as an oil, 44.2 g, 71.9% purity (70.6% yield), characterized by NMR analysis).

EXAMPLES 3–11

Preparation of 5- and/or 6-Substituted-2-hydroxy-benzoic acid esters

Using essentially the same procedure described in Examples 1 and 2 above and employing the appropriate ketoester and α,β-unsaturated aldehyde, the following 2-hydroxybenzoic acid esters shown in Table I are obtained.

TABLE I

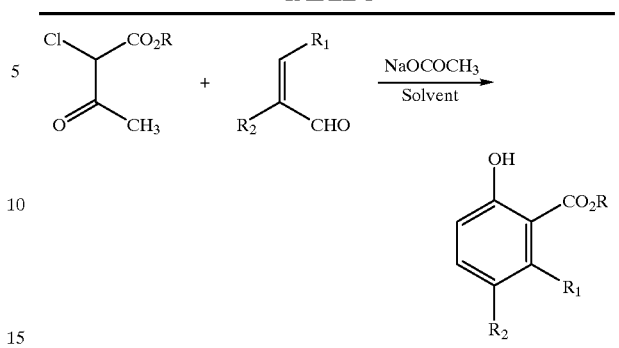

| Ex. No. | R | R1 | R2 | Solvent | % Yield |
|---|---|---|---|---|---|
| 3 | $CH_3$ | $CH_3$ | H | $CH_3CO_2H$ | 43.7 |
| 4 | Sec-Butyl | $CH_3$ | H | $CH_3CO_2H$ | 50.2 |
| 5 | $C_2H_5$ | $CH_3$ | H | n-BuOH | 44.0 |
| 6 | $C_2H_5$ | $CH_3$ | H | $C_2H_5OH$ | 37.0 |
| 7 | $C_2H_5$ | H | H | $CH_3CO_2H$ | 70.8 |
| 8 | $C_2H_5$ | H | $C_2H_5$ | $CH_3CO_2H$ | 44.0 |
| 9 | $C_2H_5$ | H | $n-C_4H_9$ | $CH_3CO_2H$ | 32.0 |
| 10 | $C_2H_5$ | $CH_3$ | $CH_3$ | $CH_3CO_2H$ | Low |
| 11 | $C_2H_5$ | $C_2H_5$ | H | $CH_3CO_2H$ | 24.6 |

EXAMPLE 12

Preparation of Ethyl 2-Hydroxy-6-methylbenzoate via 2-acetoxyacetoacetate

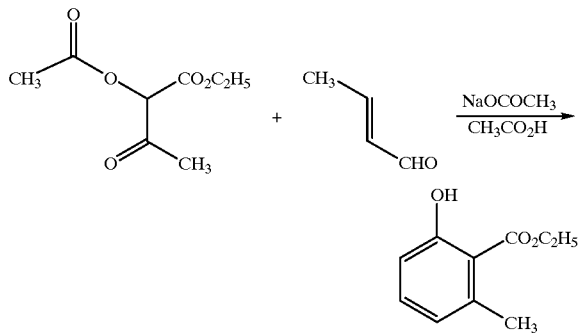

In this example, ethyl 2-acetoxyacetoacetate is prepared by heating a mixture of ethyl 2-chloroaceto-acetate (95.5 g, 95%, 0.58 mol) and sodium acetate (57.0 g, 0.7 mol) in acetic acid at reflux temperature under $N_2$ for 16 hr and concentrating the reaction mixture in vacuo to give a residue. The residue is partitioned between ethyl acetate and water. The organic phase is diluted with hexanes, washed sequentially with water and aqueous $NaHCO_3$, and concentrated in vacuo to obtain an oil, 82 g, identified as ethyl 2-acetoxyacetoacetate by NMR and mass spectral analyses.

A portion of the thus-obtained ethyl 2-acetoxyaceto-acetate (19.0 g, 0.1 mol theory) without further purification, is mixed with crotonaldehyde (10.0 g, 0.14 mole) and sodium acetate (3.0 g, 0.036 mol) in acetic acid and heated at reflux temperature for 16 hr. The reaction mixture is cooled to room temperature and concentrated in vacuo to give a residue. The residue is partitioned between ethylacetate and water. The organic phase is diluted with hexanes, washed sequentially with water and aqueous $NaHCO_3$ and concentrated in vacuo to give the title product as an oil, 16.6 g, 41% purity (37.8% yield), characterized by NMR analysis.

I claim:
1. A process for the preparation of a compound of formula I

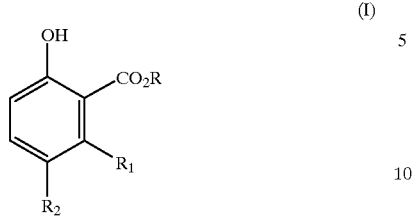

wherein
R is $C_1$–$C_6$alkyl; and
$R_1$ and $R_2$ are each independently H or $C_1$–$C_4$alkyl which process comprises reacting a compound of formula II

wherein R is $C_1$–$C_6$alkyl and X is halogen or $OCOCH_3$ with a compound of formula III

wherein $R_1$ and $R_2$ are each independently H or $C_1$–$C_4$alkyl, in the presence of a $C_1$–$C_4$carboxylic acid salt and a solvent.

2. The process according to claim 1 wherein the solvent is a $C_1$–$C_6$alkanol, a $C_1$–$C_4$carboxylic acid or a mixture thereof.

3. The process according to claim 2 wherein the solvent is methanol, ethanol, acetic acid or a mixture thereof.

4. The process according to claim 1 wherein the $C_1$–$C_4$carboxylic acid salt is a sodium or potassium salt thereof.

5. The process according to claim 4 wherein said salt is sodium acetate.

6. The process according to claim 1 having a formula II compound wherein X is halogen.

7. The process according to claim 6 having a formula II compound wherein X is Cl.

8. The process according to claim 1 having a formula III compound wherein $R_1$ is methyl and $R_2$ is H.

9. The process according to claim 5 wherein the solvent is acetic acid, ethanol or a mixture thereof.

10. The process according to claim 9 for the preparation of a formula I compound wherein R is ethyl, $R_1$ is methyl and $R_2$ is H.

11. A process for the manufacture of a fungicidal benzophenone compound of formula IV

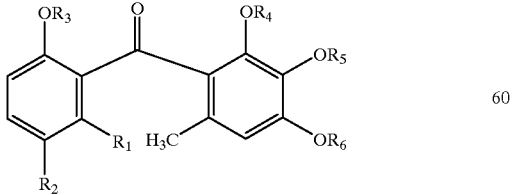

wherein $R_1$ and $R_2$ are each independently H or $C_1$–$C_4$alkyl; and $R_3$, $R_4$, $R_5$ and $R_6$ are each independently $C_1$–$C_6$alkyl which process comprises the following steps:

a) reacting a compound of formula II

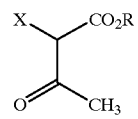

wherein R is $C_1$–$C_6$alkyl and X is halogen or $OCOCH_3$ with a compound of formula III

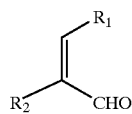

wherein $R_1$ and $R_2$ are as described hereinabove in the presence of a $C_1$–$C_4$carboxylic acid salt and a solvent to form a compound of formula I

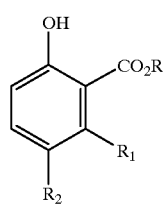

wherein R, $R_1$ and $R_2$ are described hereinabove;

b) alkylating the formula I compound with a di($C_1$–$C_6$alkyl)sulfate in the presence of a base to form a compound of formula V

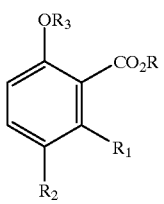

wherein $R_3$ is $C_1$–$C_6$alkyl;

c) hydrolyzing the formula V compound in aqueous acid or aqueous base to form the compound of formula VI

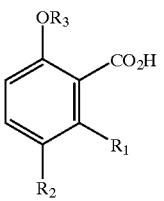

wherein $R_1$, $R_2$ and $R_3$ are described hereinabove;

d) reacting the formula VI compound with thionyl chloride to form the compound of formula VII

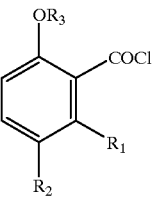

wherein $R_1$, $R_2$ and $R_3$ are described hereinabove; and e) reacting the formula VII compound with at least one molar equivalent of a compound of formula VIII

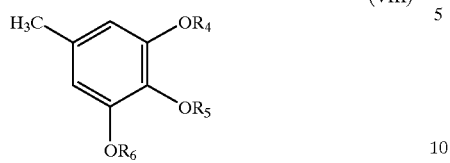
(VIII)

wherein $R_4$, $R_5$ and $R_6$ are each independently $C_1$–$C_6$ alkyl, in the presence of a Lewis acid and optionally in the presence of a solvent, to give the desired fungicidal formula IV benzophenone compound.

12. A process for the manufacture of a fungicidal benzophenone one compound of formula K

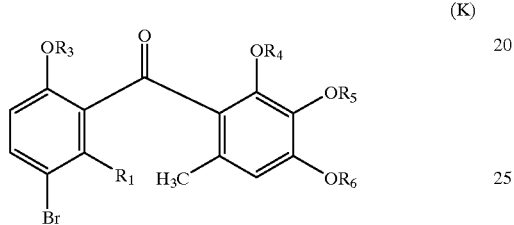
(K)

wherein $R_1$ is independently H or $C_1$–$C_4$alkyl; and $R_3$, $R_4$, $R_5$ and $R_3$, $R_4$, $R_5$ and $R_6$ are each independently $C_1$–$C_6$alkyl which process comprises the following steps:

a) reacting a compound of formula II

(II)

wherein R is $C_1$–$C_6$alkyl and X is halogen or $OCOCH_3$ with a compound of formula IIIA

(IIIA)

wherein $R_1$ is as described hereinabove in the presence of a $C_1$–$C_4$carboxylic acid salt and a solvent to form a compound of formula IA

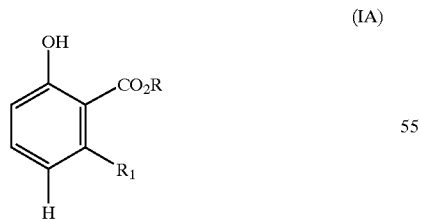
(IA)

wherein R, $R_1$ and $R_2$ are described hereinabove;

b) alkylating the formula I compound with a di($C_1$–$C_6$alkyl)sulfate in the presence of a base to form a compound of formula VA

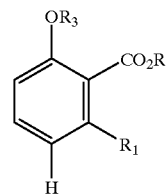
(VA)

wherein $R_3$ is $C_1$–$C_6$alkyl;

c) brominating the formula VA compound with a brominating agent optionally in the presence of a base, to form a compound of formula L

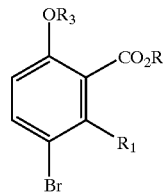
(L)

wherein R, $R_1$ and $R_3$ are described hereinabove;

d) hydrolyzing the formula L compound in an aqueous acid or aqueous base to form a compound of formula M

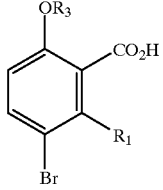
(M)

wherein $R_1$ and $R_3$ are described hereinabove;

e) reacting the formula M compound with thionyl chloride to form the compound of formula N

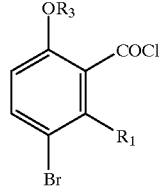
(N)

wherein $R_1$ and $R_3$ are described hereinabove; and f) reacting the formula N compound with at least one molar equivalent of a compound of formula VIII

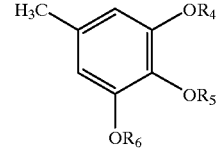
(VIII)

wherein $R_4$, $R_5$ and $R_6$ are each independently $C_1$–$C_6$alkyl, in the presence of a solvent, to give the desired fungicidal formula K benzophenone compound.

* * * * *